(12) United States Patent
Learmonth

(10) Patent No.: US 7,005,553 B2
(45) Date of Patent: Feb. 28, 2006

(54) METHOD FOR THE NITRATION OF PHENOLIC COMPOUNDS

(75) Inventor: David Alexander Learmonth, Alfena (PT)

(73) Assignee: Portela, C.A., S.A., S. Mamede do Coronado (PT)

( * ) Notice: Subject to any disclaimer, the term of this patent is extended or adjusted under 35 U.S.C. 154(b) by 66 days.

(21) Appl. No.: 10/484,405

(22) PCT Filed: Jul. 22, 2002

(86) PCT No.: PCT/GB02/03356

§ 371 (c)(1),
(2), (4) Date: May 20, 2004

(87) PCT Pub. No.: WO03/011810

PCT Pub. Date: Feb. 13, 2003

(65) Prior Publication Data

US 2004/0192961 A1     Sep. 30, 2004

(30) Foreign Application Priority Data

Jul. 25, 2001   (GB) .................................. 0118139

(51) Int. Cl.
C07C 205/06     (2006.01)

(52) U.S. Cl. ...................... 568/706; 562/475; 564/280; 564/409; 564/411

(58) Field of Classification Search ................ 562/475; 564/280, 409, 411; 568/706
See application file for complete search history.

(56) References Cited

U.S. PATENT DOCUMENTS 3,694,513 A * 9/1972 Tobey et al. ................ 568/711

FOREIGN PATENT DOCUMENTS

EP     1010688 A1     6/2000

OTHER PUBLICATIONS

Raudnitz, Harry, "Uber die Einwirkung von Athylnitrat auf Diphenyl und Diphenyl-Abkommlinge", Chem. Ber., No. 60, 1927, pp. 738-740, XP001119778.

Laali, Kenneth K. and Gettwert, Volker J., "Electrophilic Nitration of Aromatics in Ionic Liquid Solvents", J. of Organic Chem., No. 66, 2001, pp. 35-40, XP002220609.

* cited by examiner

Primary Examiner—Elvis O. Price
(74) Attorney, Agent, or Firm—Rankin, HIll, Porter & Clark LLP

(57) ABSTRACT

A method for the regioselective ortho-directed nitration of phenolic compounds useful for the preparation of ortho-nitro-phenols according to formula (I) is described.

22 Claims, No Drawings

METHOD FOR THE NITRATION OF PHENOLIC COMPOUNDS

This invention relates to a method for the nitration of phenolic compounds, which are useful for the preparation of ortho-nitro-phenols.

The nitration of aromatic compounds via electrophilic aromatic substitution is a fundamental organic reaction which has been described and reviewed extensively in the chemical literature (Olah, G. A. et al., Nitration: Methods and Mechanisms, VCH, New York, 1989 and Taylor, R., Electrophilic Aromatic Substitution, J. Wiley & Sons, Chichester, 1990). Somewhat surprisingly however, despite this wealth of information, most commercially important industrial processes still employ 'classical' technology requiring mixtures of nitric and sulphuric acid. The use of such corrosive reagents (usually in excess) creates serious environmental issues and the treatment and disposal of 'used' acids is expensive. Pertinent aspects from the viewpoint of chemistry are problems associated with over-nitration and the formation of unwanted oxidised by-products, which are often difficult to remove from the wanted product. Additionally, another serious issue with the nitration of aromatic compounds concerns the product distribution in terms of the ortho:meta:para isomer ratio (i.e. regioselectivity). It is desirable for an industrial nitration process to display a good degree of regioselectivity in this respect where regioisomer formation is possible and it is commonly the case that the para-nitro isomers in particular are the commercial products of interest. This regioselectivity is determined by steric factors and/or electronic and solvent effects. The nitration of, for example, an aromatic ring containing say, an electron-donating substituent (-alkyl, —OH, —O-alkyl etc.) normally gives rise to a mixture of predominantly ortho- and para-nitrated products, usually following a statistical distribution. Steric bulk of the nitrating reagent and/or of substituents on the aromatic ring tends to favour formation of the para-product. In many cases, the use of supported reagents and catalysts can also be employed to influence more favourably the formation of the para-isomer (Smith, K., Solid Supports and Catalysts in Organic Synthesis; Ellis Horwood: Chichester, 1992).

Logically therefore, the nitration of aromatic phenolic (Ar—OH) compounds without substituents other than hydrogen at the para-position presents particular problems where the formation of ortho- and para-products is possible due to the strongly activating effect of the electron-donating hydroxy group (where para-substituents are present, e.g. alkyl, the para-position is not available to undergo electrophilic aromatic substitution and in such cases, only ortho-nitrated products are obtained). The use of strong mixtures of acids usually gives rise to deeply-coloured and complex reaction mixtures due to oxidative degradation of the substrate. Nitration of phenol itself can be easily achieved under milder conditions using dilute nitric acid in chlorinated solvent in reasonable combined yield (61%) with a 1:2.3 ratio of ortho:para-nitrophenol isomers (Vollhardt, K. P. C. and Schore, N. E., Organic Chemistry, $2^{nd}$ ed; W. H. Freeman, New York, 1994). Nitration using sodium nitrate in sulphuric acid gives also a 61% combined yield with a ratio of 1.4:1 of ortho:para isomers (Vogel, A. I., Vogel's Textbook of Practical Organic Chemistry, $5^{th}$ ed; J. Wiley & Sons, New York, 1989). Recently, a three-step para-selective nitration of phenol derivatives was claimed (Kanno, H. et al., DE 19723214 A1) and other para-selective nitrating reagents have been reported including novel metallic nitrate dinitrogen tetroxide complexes (Firouzabadi, H. et al., Synth. Commun., 27(19), 3301–3311 (1997); Iranpoor, N. et al., Synth. Commun., 28(15), 2773–2781 (1998)), metal nitrates under non-aqueous and aprotic conditions (Firouzabadi, H. et al., Iran. J. Chem., 16(2), 48–58 (1997)) and ionic complexes of dinitrogen tetroxide with 18-crown-6 (Iranpoor, N. et al., Synth. Commun., 29(19), 3295–3302 (1999)).

Not surprisingly, far fewer methods have been described for the selective ortho-nitration of para-unsubstituted phenolic compounds. Lanthanide (III) nitrate salts in refluxing ethyl acetate was reported for the selective meta-directed nitration of 3-substituted phenols (Gu, S. et al., Synth. Commun., 27(16), 2793–2797 (1997)) but these lanthanide reagents are prohibitively expensive and the reaction itself evolves fumes of toxic nitrogen dioxide gas.

The selective ortho-directed nitration of a few phenolic compounds has received some aftention due to the potential usefulness of the products. A two-step procedure for the selective ortho-directed nitration of 3-methoxyphenol involving nitrosation followed by oxidation to give 2-nitro-5-methoxyphenol has been described (Maleski, R. J., Synth. Commun., 23(3), 343–348 (1993)) although the overall yield was relatively low and the regioselectivity of nitrosation was undoubtedly enhanced in this particular case by the presence of the strongly ortho/para-directing methoxy group (due to steric reasons, the para-position relative to the methoxy group would be favoured in this case). A single-step nitration methodology would of course be preferable to a multi-step approach. The so-called 'chaperon' effect (Strazzoloni, P. et al., Bull. Chem. Soc. Jpn., 68(4), 1155–61 (1995)) described for the selective ortho-directed nitration of alkylbenzenes could not be directly used for oxidation-sensitive phenolic compounds (Strazzoloni, P. et al., J. Org. Chem., 63(4), 952–958 (1998)). A near selective ortho-nitration of phenol using a microemulsion solution in the presence of dilute nitric acid was claimed (Chhatre, A. S. et al., J. Colloid Interface Sci., 158(1), 183–187 (1993)) but the method has obvious disadvantages for general and larger-scale preparative purposes. Very high selectivity was also observed with nitronium tetrafluoroborate and a surfactant in acetonitrile (Pervez, H. et al., Tetrahedron, 44, 4555 (1988)) but these conditions and reagents are again inconvenient for larger-scale nitrations.

Somewhat more interesting is the nitration of phenol using 'claycop', essentially clay supported cupric nitrate which is reported to afford a 92% yield of ortho-nitrophenol (Gigante, B. et al., J. Org. Chem., 60, 3445–3447 (1995)). Although highly ortho-selective (13:1, ortho:para) and high-yielding, the 'claycop' reagent is not readily available from commercial sources and is also very expensive. Preparation of the reagent is tedious, the loading (mmol reagent per gram of clay support) is low and it should be stored for only short times and at low temperature (~4° C.). Additionally it is presumed that the actual nitrating reagent itself is in fact in situ formed acetyl nitrate ($CH_3CO—ONO_2$), a known and potentially explosive compound not normally isolated. These nitration reactions are rather exothermic with uncertain induction periods and when using larger quantities, sometimes violent with strong evolution of red-brown gas. Strict safety measures must be applied when using such compounds, which due to their hazardous nature are not amenable to larger-scale preparations. A later publication described the nitration of phenol using acyl nitrates adsorbed on silica gel (Rodrigues, J. A. R. et al., Tetrahedron, 55, 6733–6738 (1999)) which was claimed to improve stability of the nitrating reagent. Although almost identical selectivity and yield was obtained as for the aforementioned 'claycop' procedure, it does not avoid the inconvenient, expensive and dangerous preparation of the acyl nitrates and requires subsequent adsorption onto silica gel. Due to the hazardous nature of these materials it would be dangerous to attempt the reaction above the 50mmol scale as indicated by the authors. Notably, although the reagent worked extremely well for phenol itself, the ortho-selectivity when applied to other phenolic compounds was considerably lower (e.g. for isovanillin, 0.6:1, ortho:para) indicating that the method is not universally regioselective. Another example of the nitration of isovanillin using 70% nitric acid in cold acetone (Napoletano, M. et al., WO 99/32449, PCT/EP98/08292) was claimed to give a 74% combined yield of nitrated isomers with only slightly improved selectivity for the ortho-nitrated product (ortho:para, 1.5:1) which was not thereafter isolated in pure form.

The utility of alkyl nitrates as potentially useful reagents for the selective ortho-directed nitration of para-un/substituted phenolic compounds has not been described in the chemical literature. One non-related report describes the combination of n-butyl nitrate and an unusual acid catalyst (Nafion-H) for the nitration of alkylbenzenes only, with clear preference for formation of the less-hindered para-nitrated product over the ortho-nitrated isomer (Olah, G. et al., J. Org. Chem., 43(24), 4628–4630 (1978)). Other drawbacks include the relatively low stability of the particular alkyl nitrate used and the use of a very expensive catalyst. The use of methyl nitrate for a similar reaction described earlier (Olah, G. et al., Synthesis, 488 (1973)) would be highly undesirable due to the potentially explosive nature of methyl nitrate. A Chinese group recently claimed a similar nitration of some alkylbenzenes using a different catalyst (zeolite HZSM-5) but again the selectivity was enhanced for the para-position (Peng, X. et al., Nanjing Ligong Daxue Xuebao, 23(6), 539–541 (1999)).

U.S. Pat. No. 3,694,513 relates to a method for nitrating alkylphenols with nitric acid in the presence of a secondary or tertiary alcohol, a secondary alkyl nitrate, an aldehyde or a ketone.

There is lacking therefore in the prior art, a safe, economical, scaleable and generally applicable nitration methodology that may be used for the high-yielding and regioselective ortho-directed nitration of phenolic compounds especially where the formation of mixtures of isomeric nitro-products and/or formation of oxidised by-products is possible.

It is an object of the invention to provide a useful, high-yielding and generally applicable method for the regioselective ortho-directed nitration of phenolic compounds. A further object of the invention is to provide a method which avoids the disadvantages of the prior art.

Such compounds are particularly useful as pharmaceutically effective compounds, or precursors or intermediates in the manufacture thereof. For instance such compounds may be used in the manufacture of catechol-O-methyl transferase (COMT) inhibitors, which are used in the treatment of central and peripheral nervous system disorders, such as Parkinson's disease.

According to one aspect of the invention there is provided a method for the preparation of compounds of formula I

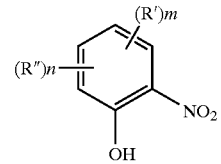

FORMULA I wherein: the terms R' and R" may be the same or different and represent: hydrogen; lower alkyl; hydroxy; lower alkoxy; halogen; the group —CO—$R^1$, wherein $R^1$ signifies hydrogen, hydroxy, alkylaryl, alkylheterocycloalkyl or optionally substituted saturated or partially unsaturated lower alkyl or aryl group, or $R^1$ signifies the group —O—$R^2$, wherein $R^2$ signifies a lower alkyl or aryl group; the group —C=N—$R^a$, wherein $R^a$ signifies $NHR^a$, wherein $R^a$ represents optionally substituted lower alkyl or aryl group, or $OR^b$ group, where $R^b$ signifies hydrogen, lower alkyl or lower alkanoyl; the group —C—$R^cR^d$, where $R^c$ signifies an optionally substituted alkylidene, where $R^d$ represents $OR^e$ group where $R^e$ signifies optionally substituted lower alkanoyl or aryl group; or R' and R" taken together signify an optionally substututed saturated or partially unsaturated carbocyclic ring; m and n are independently 0, 1 or 2; the term lower alkyl means a carbon chain, straight or branched, containing from one to six carbon atoms; the term halogen means fluorine, chlorine, bromine or iodine; the term heterocycloalkyl means a five or six-membered cyclic ring incorporating one or two atoms of oxygen, sulphur or nitrogen; the term aryl means a phenyl or naphthyl group optionally substituted by alkoxy, halo or nitro groups; said method comprising reacting a phenolic compound of formula II:

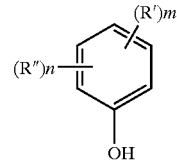

FORMULA II wherein the terms R' and R", m and n are defined above, with an alkyl nitrate of formula (III)

FORMULA III where $R^3$ represents an alkyl group straight or branched, containing preferably from one to sixteen carbon atoms, or $R^3$ represents a cycloalkyl group containing either five or six carbon atoms.

The reaction is preferably carried out in the presence of an acid catalyst in a substantially inert solvent.

Preferred alkyl nitrates include isopropyl nitrate, isoamyl nitrate and isooctyl nitrate (2-ethylhexyl nitrate). Compounds of formula (III) are known and many are commercially available, or they can be made by those skilled in the art (e.g. Olah, G. et al., Synthesis, (2), 207–208 1993)). The nitration reaction may be carried out by stirring the phenolic compound of formula II with usually an excess of the preferred alkyl nitrate (1.2–2.5 molar equivalents) in inert solvents such as hydrocarbons, chlorinated alkanes, ethers or aprotic dipolar solvents, or the reaction can be run in a mixture of the above mentioned solvents. The reaction is run with the use of mineral or organic acid catalysts such as, for example, sulphuric acid (concentration 20–96%), hydrochloric acid, phosphoric acid, formic acid or trifluoroacetic acid, neat, or if preferred, adsorbed onto inert supports such as for example, silica gel. Alternatively a Lewis acid may be used, such as for example, boron trifluoride etherate. If desired, the reaction may be run using a phase-transfer co-catalyst such as a tetraalkylammonium halide or hydrogensulphate salt (1–5 mol%). The reaction may be performed at various temperatures and pressures e.g. between 0° C. and the boiling temperature of the reaction mixture at the pressure used. The reaction product/s may be simply isolated after washing the reaction mixture with water and evaporation of the reaction solvent. If necessary, separation of the major ortho-nitrated product from any minor nitro-isomer contaminants or by-products present in the crude product can be rapidly achieved by distillation or chromatography on a suitable stationary phase such as silica gel or alumina, using an appropriate solvent system for elution. More conveniently, the crude product may be recrystallised from a suitable solvent in which the wanted ortho-nitrated product has more limited solubility than any contaminating nitro-isomers or by-products. The purified products may then be characterised by analytical comparison with authentic standards (e.g. TLC) and/or the position of nitration can be rapidly determined by NMR spectroscopy. An advantage of this method is that it is high yielding; the overall yield of this nitration reaction frequently exceeding 75%. Another advantage of this method is that it is regioselective, with the regioselectivity favouring predominant formation of the ortho-nitrated product.

For avoidance of doubt, it is stated that in formula I, R' and R" may be substituted on any position on the phenyl group.

Additionally, it is envisioned that compounds represented by formula I may be used as precursors or intermediates in the production of further pharmaceutically active/effective compounds. According to another aspect of the invention there is provided a method for the reparation of a compound of formula IV:

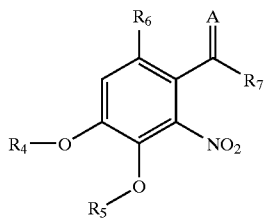

FORMULA IV where $R_4$ and $R_5$ are the same or different and signify hydrogen, optionally substituted lower alkanoyl or aroyl, optionally substituted lower alkoxycarbonyl, or optionally substituted lower alkylcarbamoyl; $R_6$ signifies hydrogen or optionally substituted alkanoyl or aroyl group; $R_7$ signifies optionally substituted saturated or partially unsaturated lower alkyl or aryl group, or taken together with $R_6$ signifies an optionally substituted saturated or partially unsaturated carbocyclic ring; A signifies oxygen or $NR_8$ group, where $R_8$ signifies $NHR_9$ where $R_9$ signifies optionally substituted lower alkyl or aryl group, or $OR_{10}$ group where $R_{10}$ signifies hydrogen, lower alkyl or lower alkanoyl, or A signifies an optionally substituted alkylidene when $R_7$ signifies $OR_{11}$ group where $R_{11}$ signifies optionally substituted lower alkanoyl or aroyl group, and pharmaceutically acceptable salts thereof; said method comprising the steps of: taking a compound of formula I manufactured in accordance with the method described above, and treating said compound to produce a compound of formula IV.

In one embodiment of these further methods, the treatment may comprise a dealkylation step, which may be a demethylation step. In another embodiment, the treatment may comprise an acylation step. Preferably, the treatment comprises both a dealkylation step and an acylation step.

In a preferred embodiment of this method, m=1, n=1, wherein R' is $COR^1$, wherein $R^1$ represents phenyl, and R" is methoxy. Preferably the compound of formula I is treated with a demethylation step and an acylation step.

In another preferred embodiment, $R_4$ and $R_5$ are both butyryl; $R_6$ is hydrogen; $R_7$ is phenyl; and A is oxygen.

The demethylation step preferably comprises reacting the compound of formula I with a methyl-acceptor in the presence of a catalyst, and crystallizing the demethylated product. The compound of formula I may be dispersed in an organic solvent, such as ethyl acetate, 1,2-dichloroethane, dichloromethane or 1,1,2,2-tetrachloroethane. The methyl-acceptor may be pyridine and the catalyst may be aluminium chloride. Alternatively, the methyl-acceptor and catalyst may be the same compound, such as pyridinium chloride. The reaction may occur in the presence of an inert gas, such as argon. Subsequently, acid, such as HCl, may be added to the reaction mixture. The addition of acid may quench the reaction. The precipitated solid may be removed by filtration, and is preferably washed and recrystallised.

The acylation step preferably comprises reacting the demethylated compound with one or more acyl-donors, such as butyric anhydride or ethylchloroformate, optionally in the presence of pyridine, and a catalyst, such as 4-dimethylaminopyridine. The reaction may be allowed to proceed, preferably for around two hours, before the product is washed and dried. The washing step is preferably carried out with acid and brine. The residue may be filtered and evaporated in vacuo, and then recrystallised, preferably from an organic solvent/petroleum ether mixture to leave the crystallized product.

A number of the moieties in formulas I, II and IV are said to be "optionally substituted", and the methods of the invention are applicable to a wide range of possible substitutions. Particular optional substituents for the moieties include lower alkyl, alkoxy, halogen, nitro, amino or cyano. Thus, in this specification the term "optionally substituted" should be read, in a preferred embodiment as "optionally substituted with lower alkyl, alkoxy, halogen, nitro, amino or cyano."

The invention disclosed herein is exemplified by the following examples of preparation, which should not be construed to limit the scope of the disclosure. It is to be understood that the invention is not to be limited to the exact details of operation or structures shown, as obvious modifications and equivalents will be apparent to those skilled in the art. Examples 1–7 are examples of the nitration procedure. Example 8 is an example of a demethylation procedure. Example 9 is an example of an acylation procedure. Alternative dealkylation and acylation procedures, reactants and quantities are readily available to those skilled in the art (see for example the Applicant's publications GB2344819A, EP-A-1167341 & EP-A-1167341).

EXAMPLE 1

2-Nitrophenol

To a stirred solution of phenol (0.94 g, 10 mmol) in dichloromethane (10 mL) at room temperature was added tetrabutylammoniumhydrogen sulphate (0.17 g, 5 mol %) followed by isopropyl nitrate (2.63 g, 25 mmol). Sulphuric acid (96%, 0.94 mL) was then added dropwise and the mixture became darker in appearance as the reaction temperature increased gently. After five minutes, the reaction mixture was poured onto water (30 mL) and the phases were separated. The organic phase was washed with brine and dried over anhydrous sodium sulphate. Filtration and evaporation (40° C., water aspirator pressure) afforded a dark oil which was chromatographed over silica gel using a petroleum ether/ethyl acetate (4:1-3:1-2:1) solvent mixture for gradient elution. The faster-running component was isolated in pure form from the column as yellow-orange crystals (0.9 g, 65%) of m.p. 45–46° C. and which was identified by NMR spectroscopy as the ortho-nitrated title product, 2-nitrophenol (lit. m.p. 44–45° C., Merck Index No. 6541). The slower-running component thereafter recovered from the column was recrystallised from a dichloromethane/petroleum ether mixture to give pale red crystals (0.22 g, 16%) of m.p. 112–113° C. which was identified by NMR spectroscopy as the para-nitrated product, 4-nitrophenol (lit. m.p. 113–114° C., Merck Index No. 6542). (81% combined yield, Ortho:Para selectivity, 4:1).

EXAMPLE 2

3-Hydroxy4-methoxy-2-nitrobenzaldehyde

To a stirred suspension of 3-hydroxy4-methoxybenzaldehyde (isovanillin, 0.76 g, 5 mmol) in dichloromethane (10 mL) at room temperature was added tetrabutylammoniumhydrogen sulphate (0.085 g, 5 mol %) followed by isopropyl nitrate (1.31 g, 12.5 mmol). Sulphuric acid (96%, 0.76 mL) was then added dropwise to the mixture which was allowed to stir at room temperature for thirty minutes and then poured onto water (50 mL). The phases were separated and the organic layer was washed with brine and dried over anhydrous sodium sulphate. Filtration and evaporation of the solvent (40° C., water aspirator pressure) afforded a solid residue which was recrystallised from a dichloromethane/petroleum ether mixture to give orange crystals (0.74 g, 75%) of m.p. 139–140° C., identified by NMR as the ortho-nitrated title product. After concentration of the mother liquors, there was obtained a small quantity of dark orange crystals (0.11 g, 11%), corresponding (TLC) to a standard of the para-nitrated product, 3-hydroxy4-methoxy-6-nitrobenzaldehyde. (86% combined yield, Ortho:Para selectivity, 6.8:1)

EXAMPLE 3

3-Hydroxy-4-methoxy-2-nitrobenzophenone

To a stirred solution of 3-hydroxy-4-methoxybenzophenone (10.0 g, 43.8 mmol) in dichloromethane (100 mL) at room temperature was added tetrabutylammoniumhydrogen sulphate (0.74 g, 5 mol %) followed by isopropyl nitrate (11.5 g, 87.6 mmol). Sulphuric acid (96%, 10 mL) was then added dropwise causing a gently exothermic reaction, and, after stirring for forty minutes, the reaction mixture was poured onto water (300 mL). The phases were separated and the aqueous phase was extracted by dichloromethane (30 mL). The combined organic phases were washed with brine and dried over anhydrous sodium sulphate. Filtration and evaporation of the solvent (40° C., water aspirator pressure) afforded a solid residue which was recrystallised from a small volume of ethanol (96%, 10 mL) to afford yellow crystals, (7.97 g, 67%) of m.p. 137–139° C., identified by NMR as the ortho-nitrated title product. Concentration of the mother liquors and subsequent chromatography on silica gel using a petroleum ether:ethyl acetate solvent mixture (2:1) allowed the isolation of a small amount of a minor product, corresponding (TLC) to a standard of the para-nitrated product, 3-hydroxy4-methoxy-6-nitrobenzophenone (1.43 g, 12%), m.p. 154–156° C. (79% combined yield, Ortho:Para selectivity, 5.6:1)

EXAMPLE 4

1-(3-Hydroxy-4-methoxy-2-nitrophenyl)-2-phenyl-ethanone

To a stirred solution of 1-(3-hydroxy4-methoxyphenyl-2-phenyl-ethanone (8.57 g, 35.4 mmol) in dichloromethane (90 mL) at room temperature was added tetrabutylammonium sulphate (0.6 g, 5 mol %) followed by isopropyl nitrate (7.44 g, 70.8 mmol). Sulphuric acid (96%, 8.5 mL) was then added dropwise causing a gently exothermic reaction, and after stirring for forty minutes, the reaction mixture was poured onto water (250 mL). The phases were separated and the aqueous phase was extracted by dichloromethane (30 mL). The combined organic phases were washed with brine and dried over anhydrous sodium sulphate. Filtration and evaporation of the solvent (40° C., water aspirator pressure) afforded a solid residue which was triturated with a small volume of diethylether (20 mL) to afford orange crystals, (6.9 g, 68%) of m.p. 176–177° C., identified by NMR as the ortho-nitrated title product. Concentration of the mother liquors and subsequent trituration with diethyl ether (15 mL) allowed the isolation of a small amount of a minor product, which was recrystallised from a dichloromethane/heptane mixture to give yellowish crystals of m.p. 142–143° C., corresponding (TLC) to a standard of the para-nitrated product, 1-(3-hydroxy-4-methoxy-6-nitrophenyl)-2-phenyl-ethanone (1.22 g, 12%). (80% combined yield, Ortho:Para selectivity, 5.7:1)

EXAMPLE 5

2-Hydroxy-3-nitrobenzoic acid (3-Nitrosalicylic acid)

To a stirred suspension of salicylic acid (0.69 g, 5 mmol) in dichloromethane (10 mL) at room temperature was added tetrabutylammoniumhydrogen sulphate (0.085 g, 5 mol %) followed by isopropyl nitrate (1.31 g, 12.5 mmol). Sulphuric acid (96%, 0.69 mL) was then added dropwise to the mixture which was allowed to stir at room temperature for thirty minutes (became a yellow solution, followed by formation of a yellow precipitate) and then poured onto water (50 mL). The yellow precipitate was filtered off and then triturated with water (10 mL). The insoluble material was filtered off and dried to afford yellow crystals, (0.42 g, 46%) of m.p. 121–122° C. identified by NMR as the title compound (lit. m.p. 123° C., Merck Index No. 6553). The mother liquors were concentrated on a rotary evaporator (60° C., water aspirator pressure) and recrystallised from a dichloromethane/petroleum ether mixture to give yellow/orange crystals (0.35 g, 39%) of m.p. 226–228° C., identified by NMR as 2-hydroxy-5-nitrobenzoic acid (5-nitrosalicylic acid) (lit. m.p. 228–230° C., Merck Index No. 6554). (85% combined yield, Ortho:Para selectivity, 1.2:1)

EXAMPLE 6

3-Hydroxy-2-nitrobenzaldehyde and 3-hydroxy4-nitrobenzaldehyde

To a stirred suspension of 3-hydroxybenzaldehyde (0.61 g, 5 mmol) in dichloromethane (10 mL) at room temperature was added tetrabutylammoniumhydrogen sulphate (0.085 g, 5 mol%) followed by isopropyl nitrate (1.31 g, 12.5 mmol). Sulphuric acid (96%, 0.61 mL) was then added dropwise to the mixture causing a gentle rise in temperature. The reaction mixture was then stirred for fifteen minutes (became a dark brown suspension) and then poured onto water (50 mL). The phases were separated and the aqueous phase was extracted by dichloromethane (10 mL). The combined organic layers were washed by brine, dried over anhydrous sodium sulphate and filtered. Evaporation of the solvent (40° C., water aspirator pressure) afforded a brown solid which was then chromatographed over silica gel using a petroleum ether/ethyl acetate solvent mixture (2:1). The faster-running component was obtained from the column as a yellow solid (0.19 g, 23%), identified by NMR as 3-hydroxy-4-nitrobenzaldehyde. The slower-running component was also isolated as a yellow solid, identified by NMR as 3-hydroxy-2-nitrobenzaldehyde (0.56 g, 67%). (90% combined yield, both products are ortho-nitrated, no para-nitro isomer was detected).

EXAMPLE 7

2,4-Difluoro-6-nitrophenol

To a stirred solution of 2,4-difluorophenol (0.65 g, 5 mmol) in dichloromethane (7 mL) at room temperature was added tetrabutylammoniumhydrogen sulphate (0.085 g, 5 mol %) followed by isopropyl nitrate (1.31 g, 12.5 mmol). Sulphuric acid (96%, 0.65 mL) was then added dropwise to the mixture causing gentle reflux of the solvent. The reaction mixture was then stirred for fifteen minutes and then poured onto water (50 mL). The phases were separated and the aqueous phase was extracted by dichloromethane (10 mL). The combined organic layers were washed by brine, dried over anhydrous sodium sulphate and filtered through a short pad of silica gel. Evaporation of the solvent (40° C., water aspirator pressure) afforded a yellow solid, identified by NMR as the title compound (0.73 g, 83%). (ortho-selectivity 100%, no nitro-isomers detected).

EXAMPLE 8

3,4-dihydroxy-2-nitrobenzophenone

To a stirred suspension of 3-Hydroxy4-methoxy-2-nitrobenzophenone (8.3 g, 30.38 mmol) in 1,2-dichloroethane (100 ml) at room temperature under argon was added aluminium chloride (4.46 g, 33.45 mmol) in one portion followed by pyridine (9.61 g, 9.81 ml, 121.5 mmol) giving rise to an exothermic reaction. the mixture was stirred at reflux for one hour, allowed to cool to room temperature and then poured onto ice-water (300 ml). Hydrochloric acid (2N, 70 ml) was added and the mixture was stirred for one hour (initial orange precipitate gradually became yellow in appearance. The solid was removed by filtration, washed by water (30 ml) and dried under vacuum to give the product as a yellow solid 6.99 g, (89%) of melting point 153–155° C. The organic phase of the filtrate was separated and the aqueous phase was extracted by dichloromethane (20 ml). The combined organic phases were washed by brine (30 ml), dried over anhydrous sodium sulphate and the solvent removed on a rotary evaporator (bath temp. 40° C.) to leave a yellow solid (0.7 g) which was not purified further.

EXAMPLE 9 butyric acid, 3-benzoyl-6-butyrloxy-2-nitro-phenyl ester[3,4-dibutyryloxy-2-nitrobenzophenone]

To a stirred solution of (3,4-dihydroxy-2-nitro-phenyl)-phenyl-methanone (0.34 g, 1.29 mmol) (5 mL) [3,4-dihydroxy-2-nitrobenzophenone in dichloromethane] at room temperature was added pyridine (0.41 g, 5.19 mmol), butyric anhydride (0.82 g, 5.19 mmol) and 4-dimethyl-aminopyridine (0.01 g). The resulting solution was stirred for one hour and then extracted by cold water, 1N HCl and brine, then dried over sodium sulphate. After filtration and evaporation in vacuo the residue was chromatographed over silica gel using an ethyl acetate/petroleum ether mixture to give off-white crystals of m.p 55 to 57° C.

It will be appreciated that the invention described above may be modified.

The invention claimed is:

1. A method for the preparation of compounds of formula I

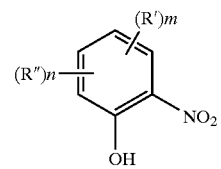

FORMULA I wherein: the terms R' and R" may be the same or different and represent: hydrogen; lower alkyl; hydroxy; lower alkoxy; halogen; the group —CO—R$^1$, wherein R$^1$ signifies hydrogen, hydroxy, alkylaryl, alkylheterocycloalkyl or optionally substituted saturated or partially unsaturated lower alkyl or aryl group, or R$^1$ signifies the group —O—R$^2$, wherein R$^2$ signifies a lower alkyl or aryl group; the group —C=N—R$^a$, wherein R$^a$ signifies NHR$^a$, wherein R$^a$ represents optionally substituted lower alkyl or aryl group, or OR$^b$ group, where R$^b$ signifies hydrogen, lower alkyl or lower alkanoyl; the group —C—R$^c$R$^d$, where R$^c$ signifies an optionally substituted alkylidene, where R$^d$ represents OR$^e$ group where R$^e$ signifies optionally substituted lower alkanoyl or aryl group; or R' and R" taken together signify an optionally substituted saturated or partially unsaturated carbocyclic ring; m and n are independently 0, 1 or 2; the term lower alkyl means a carbon chain, straight or branched, containing from one to six carbon atoms; the term halogen means fluorine, chlorine, bromine or iodine; the term heterocycloalkyl means a five or six-membered cyclic ring incorporating one or two atoms of oxygen, sulphur or nitrogen; the term aryl means a phenyl or naphthyl group optionally substituted by alkoxy, halo or nitro groups; said method comprising reacting a phenolic compound of formula II:

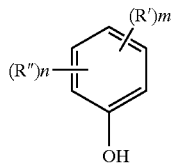

FORMULA II wherein the terms R' and R", m and n are defined above, with an alkyl nitrate of formula III

FORMULA III where $R^3$ represents an alkyl group straight or branched, containing from one to sixteen carbon atoms, or $R^3$ represents a cycloalkyl group containing either five or six carbon atoms, said reaction of the phenolic compound of formula II with the alkyl nitrate of formula III being carried out in the presence of an acid catalyst.

2. The method according to claim 1, wherein the acid catalyst is a mineral acid or an organic acid.

3. The method according to claim 1, wherein the acid catalyst is sulphuric acid.

4. The method according to claim 1, wherein the acid catalyst is a Lewis acid catalyst.

5. The method according to claim 1 wherein the alkyl nitrate is isopropyl nitrate.

6. The method according to claim 1 wherein the alkyl nitrate is isobutyl nitrate.

7. The method according to claim 1 wherein the alkyl nitrate is isoamyl nitrate (isopentyl nitrate).

8. The method according to claim 1 wherein the alkyl nitrate is isooctyl nitrate (2-ethylhexyl nitrate).

9. The method according to claim 1 wherein the phenolic compound is 3-hydroxy4-methoxybenzophenone.

10. The method according to claim 1, wherein R' and R" may be the same or different and signify saturated or partially unsaturated lower alkyl or aryl group, optionally substituted with lower alkyl, alkoxy, halogen, nitro, amino or cyano.

11. A method according to claim 1, for preparing a compound of formula IV:

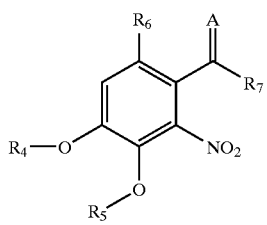

FORMULA IV where $R_4$ and $R_5$ are the same or different and signify hydrogen, optionally substituted lower alkanoyl or aroyl, optionally substituted lower alkoxycarbonyl, or optionally substituted lower alkylcarbamoyl; $R_6$ signifies hydrogen or optionally substituted alkanoyl or aroyl group; $R_7$ signifies optionally substituted saturated or partially unsaturated lower alkyl or aryl group, or taken together with $R_6$ signifies an optionally substituted saturated or partially unsaturated carbocyclic ring; A signifies oxygen or $NR_8$ group, where $R_8$ signifies $NHR_9$ where $R_9$ signifies optionally substituted lower alkyl or aryl group, or $OR_{10}$ group where $R_{10}$ signifies hydrogen, lower alkyl or lower alkanoyl, or A signifies an optionally substituted alkylidene when $R_7$ signifies $OR_{11}$, group where $R_{11}$ signifies optionally substituted lower alkanoyl or aroyl group, and pharmaceutically acceptable salts thereof; wherein said method comprises the step of: taking a compound of formula I, and treating said compound to produce a compound of formula IV.

12. The method according to claim 11, wherein the phenolic compound of formula II is 3-hydroxy4-methoxybenzophenone, and the intermediate compound of formula I is 3-hydroxy4-methoxy-2-nitrobenzophenone.

13. The method according to claim 11, wherein the compound of formula IV is butyric acid, 3-benzoyl-6-butyryloxy-2-nitrophenyl ester.

14. The method according to claim 11, wherein the treatment comprises a dealkylation step.

15. The method according to claim 11, wherein the dealkylation step comprises a demethylation step.

16. The method according to claim 15, wherein the demethylation step comprises reacting the compound of formula I with a methyl acceptor, in the presence of a catalyst, and recrystallizing the demethylated product.

17. The method according to claim 11, wherein the treatment comprises an acylation step.

18. The method according to claim 17, wherein the acylation step comprises reacting the compound of formula I, or its demethylated equivalent with an acyl-donor in the presence of a catalyst.

19. The method according to claim 11, wherein m=1, n=1, R' is $-COR^1$, wherein $R^1$ represents phenyl, and R" is a methoxy group; the treatment comprising a demethylation step and an acylation step.

20. The method according to claim 19, wherein $R_4$ and $R_5$ are both butyryl; $R_6$ is hydrogen; $R_7$ is phenyl; and A is oxygen.

21. The method according to claim 15, wherein the demethylation step comprises reacting the compound of formula I with a methyl acceptor, in the presence of a catalyst selected from the group consisting of aluminum chloride and pyridinium chloride, and recrystallizing the demethylated product.

22. The method according to claim 17, wherein the acylation step comprises reacting the compound of formula I, or its demethylated equivalent with an acyl-donor in the presence of a 4-dimethyl-aminopyridine catalyst.

* * * * *